United States Patent [19]

Welter

[11] Patent Number: 4,720,559
[45] Date of Patent: Jan. 19, 1988

[54] CERTAIN 2,3-DIHYDOBENZOFURAN-3-YL ACETIC ACIDS AND THEIR METHOD OF PREPARATION

[75] Inventor: Thomas R. Welter, Webster, N.Y.

[73] Assignee: Eastman Kodak Company, Rochester, N.Y.

[21] Appl. No.: 916,975

[22] Filed: Oct. 9, 1986

[51] Int. Cl.$^4$ ............................................. C07D 307/80
[52] U.S. Cl. ..................................... 549/462; 549/469
[58] Field of Search ................................. 549/462, 469

[56] References Cited

U.S. PATENT DOCUMENTS 3,917,600  11/1975  Descamps et al. ................... 549/467

FOREIGN PATENT DOCUMENTS 551407  5/1974  Switzerland .

OTHER PUBLICATIONS

J. Indian Chem. Soc., vol. 57, No. 6, pp. 633–636 (1980), J. N. Chatterjea and Radhika Pati Sahai.
J. Med. Chem., vol. 22, pp. 699–705 (1979) Donald T. Witiak et al.

Primary Examiner—Henry R. Jiles
Assistant Examiner—Bernard I. Dentz

Attorney, Agent, or Firm—Dana M. Schmidt

[57] ABSTRACT

There are disclosed novel benzofurans having the following structural formula:

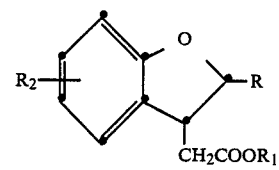

wherein R is alkenyl of 1 to 6 carbon atoms or aryl of from 6 to 10 carbon atoms; $R_1$ is H, alkali metal, or alkyl of 1 to 4 carbon atoms; and $R_2$ is alkyl or alkoxy of from 1 to 5 carbon atoms, hydrogen, amino or dialkylamino, nitro, sulfonyl, alkyl or aryl thioether or halide. Also disclosed is a novel process of making the benzofurans, comprising the step of cyclizing an o-(2-carboxyvinyl)-phenyl unsaturated alkyl ether in the presence of a base selected from the group consisting of KOH, NaOH, LiOH, dimsyl sodium, lithium diisopropylamide, potassium tert-butoxide, and mixtures thereof, at room temperature.

5 Claims, No Drawings

CERTAIN 2,3-DIHYDOBENZOFURAN-3-YL ACETIC ACIDS AND THEIR METHOD OF PREPARATION

FIELD OF THE INVENTION

This invention relates to novel benzofurans and a process of preparing them.

BACKGROUND OF THE INVENTION

Certain heterocyclic compounds have been found to be useful starting materials in preparing acetamidine derivatives having pharmacological activity. For example, U.S. Pat. No. 3,917,600 granted Nov. 4, 1975, describes the following compound as a starting material:

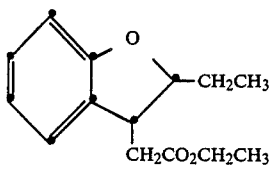

A

By a series of complex reactions, this is converted into an acetamidine derivative having antihypertensive activity.

Additional benzofurans as starting material in preparing acetamidine derivatives having pharmacological activity have been desired prior to this invention, so that alternative modes of preparation are available.

SUMMARY OF THE INVENTION

This invention is based on the discovery that novel benzofurans can be produced to use as starting materials to make the acetamidine derivatives described above.

More specifically, in accord with one aspect of the invention there is provided a benzofuran having the following structural formula:

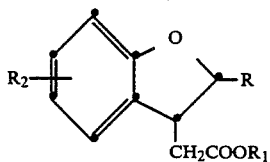

wherein R is alkenyl of 2 to 6 carbon atoms or aryl of from 6 to 10 carbon atoms; $R_1$ is H, alkali metal, or alkyl of 1 to 4 carbon atoms; and $R_2$ is alkyl or alkoxy of from 1 to 5 carbon atoms, hydrogen, amino or dialkylamino, nitro, sulfonyl, alkyl or aryl thioether wherein the aryl group contains 6 to 10 carbon atoms, or halo.

In accord with another aspect of the invention, there is provided a method of forming a benzofuran comprising the step of cyclizing an o-(2-carboxyvinyl)phenyl unsaturated alkyl ether in the presence of a base selected from the group consisting of KOH, NaOH, LiOH, dimsyl sodium, potassium tert-butoxide, lithium diisopropylamide, and mixtures thereof, at room temperature.

Thus, it is an advantageous feature of the invention that novel starting materials are provided which are useful to make acetamidines having antihypertensive activity.

It is another advantageous feature of the invention that such starting materials have pharmacological activity.

Still another advantageous feature of the invention is the preparation of such novel compounds by the step of cyclizing with base.

Other advantageous features will become apparent upon reference to the following description of the preferred embodiments.

DESCRIPTION OF THE PREFERRED EMBODIMENTS

I have discovered novel benzofurans having the structure set forth in the Summary above. R in such structure is either alkenyl of 2 to 6 carbon atoms such as allyl, 1- or 2-butene, and the like; or aryl of 6 to 10 carbon atoms, e.g., phenyl or naphthyl. As used herein, "aryl" means unsubstituted aryl or aryl substituted with alkyl or alkoxy of 1–5 carbon atoms; amino or dialkylamino; nitro; sulfonyl; alkyl thioether of 1 to 6 carbon atoms or aryl thioether wherein the aryl group contains 6 to 10 carbon atoms; or halo such as chloro, bromo, & fluoro. $R_1$ is hydrogen; alkali metal such as lithium, sodium, potassium and the like; or alkyl of 1 to 4 carbon atoms, for example, methyl, ethyl, propyl, isopropyl and n-butyl. $R_2$ is either hydrogen or one of the substituents listed above for aryl substituents.

The most preferred examples of the benzofurans of this invention are as follows:

cis or trans-3-carboxymethyl-2-phenyl-2,3-dihydrobenzo[b]furan;

cis or trans-3-carboxymethyl-2-vinyl-2,3-dihydrobenzo[b]furan;

cis or trans-3-ethoxycarbonyl-2-phenyl-2,3-dihydrobenzo[b]furan,

These compounds are useful as intermediates in producing acetamidine derivatives of the type, or similar to those, described in the aforesaid U.S. Pat. No. 3,917,600. That is, the dihydrobenzofurans can be readily oxidized to the benzofurans by conventional techniques. Thereafter, the conversion technique is that which is described in that patent, such as, converting the benzofurans of this invention to the acid chloride, reacting the acid chloride with ammonia, and dehydrating to the nitrile using phosphorus oxychloride. Thereafter, the acetamidine is formed as per the '600 patent, using a secondary cyclic amine. Such acetamidine derivatives have antihypertensive activity, as described in the aforesaid '600 patent.

In addition, the compounds of this invention are believed to be useful in and of themselves for their pharmacological activity. As used herein, "pharmacological activity" refers to one or more of the following:

Antianxiety activity, muscle relaxant activity, sedative activity, antipsychotic activity, anticonvulsant activity, analgesia activity, antineurodegenerative activity, antihypertensive activity, anti-isthemic activity, gastrointestinal activity, regulation of GI motility, antiobesity activity, antidiabetic activity, antiasthmatic activity, and anticholinergic activity..

In accord with another aspect of the invention, the compounds of this invention are produced by the following novel process. An o-(2-carboxyvinyl)phenyl unsaturated alkyl ether, such as allyl or benzyl ether, is cyclized, preferably at room temperature, by treating with base such as KOH, lithium diisopropylamide, potassium tert-butoxide, LiOH, NaOH or dimsyl sodium [the salt formed by reacting sodium hydride in dimethyl sulfoxide (hereinafter DMSO)]using a solvent such as dimethyl sulfoxide or tetrahydrofuran, for a time ranging from about 30 min to 3 or more days, depending on the base/solvent combination employed. Thus, use of KOH as the base requires a longer reaction time. (Other strong bases will also work.)

The product so formed is isolated by conventional procedures.

The following examples are illustrative:

EXAMPLE 1:

trans-3-carboxymethyl-2-phenyl-2,3-dihydrobenzo[b]furan

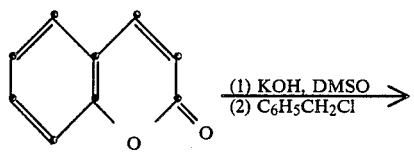

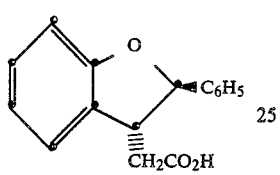

A slurry of coumarin (14.6 g, 0.10 mol), dimethyl sulfoxide (300 mL), and potassium hydroxide pellets (83 g, 1.48 mol) was stirred 5 hours at ambient temperature, then was treated with benzyl chloride (11.5 mL, 0.10 mol), in the manner taught by S. K. Kaul et al, *Indian J. Chem.*, Vol. 21B, p. 472 (1982). The resultant mixture was stirred 3 days to allow cyclization and then poured into ice water. The mixture was filtered through Celite diatomaceous earth and acidified (pH<3) with hydrochloric acid. The solid was filtered, air dried, then recrystallized from toluene to give 13.3 g (52%) of a colorless solid, mp 154°–155° C.

Anal: (fd(calc)) C 75.6 (75.3); H 5.5 (5.4).

The stereo chemistry was confirmed by Europium shift and NOE experiments. The NMR and IR spectra were consistent with the assigned structure.

PREPARATION 1:

2′-benzyloxy-E-cinnamic acid (Intermediate)

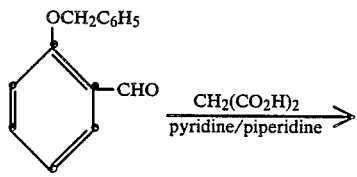

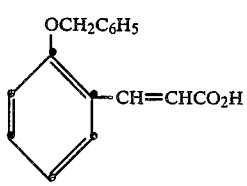

This is prepared generally by the procedure of J. Koo et al, *Org. Synthesis Coll. Vol.*, Vol. 4, p. 327 (1963). Malonic acid (20.8 g, 0.20 mol) dissolved in 40 mL pyridine at 55° C. was treated sequentially with 2-benzyloxybenzaldehyde (21.2 g, 0.10 mol) and 1.5 mL piperidine. The solution was warmed to reflux, held there until gas evolution ceased, and then poured into water. The aqueous solution was acidified (pH<3) with hydrochloric acid, the solid collected, briefly air dried, and then recrystallized from ethanol to yield a colorless solid (18.8 g, 73.9%), mp 136°–138° C.

Anal: (fd(calc)) C 75.6 (75.6); H 5.6 (5.5).

EXAMPLE 2:

cis-carboxymethyl-2-phenyl-2,3-dihydrobenzo[b]furan

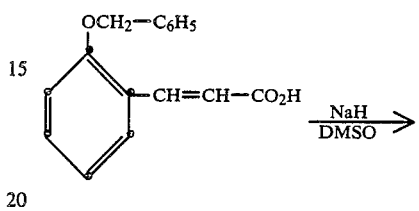

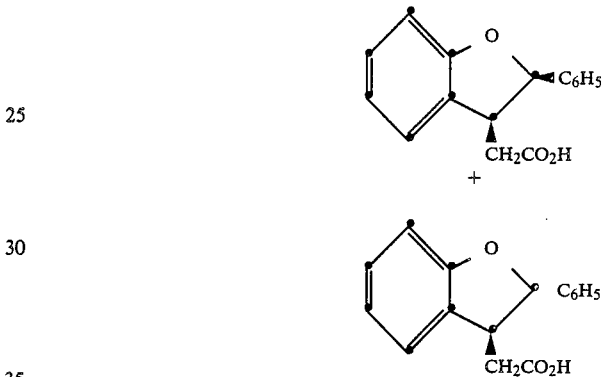

A slurry of sodium hydride (2.30 g 50% dispersion, 0.048 mol) was warmed to 70° C. in 50 mL dimethyl sulfoxide until gas evolution ceased. The solution was cooled to ambient temperature, then treated over 2 minutes with 2′-benzyloxy-E-cinnamic acid from Preparation 1 (2.54 g, 0.010 mol) in 10 mL dimethyl sulfoxide. After 30 minutes of cyclizing, the mixture was poured into ice water. Extractive ethyl acetate workup gave a colorless solid (2.52 g). Recrystallization from 30 mL toluene gave a colorless solid (1.24 g, 48.8%), mp 153°–155° C.

The mother liquors from the recrystallization were concentrated in vacuo. The residual solid was recrystallized from 15 mL toluene to afford a colorless solid (0.32 g, 13%), mp 160°–161° C.

Anal: (fd(calc)) C 75.9 (75.6); H 5.8 (55).

The lower melting product proved to be identical to the previously prepared cyclized acid.

The higher melting product was identified as the cis-fused isomer.

PREPARATION 2:

2-allyloxy-Z-cinnamic acid (Intermediate)

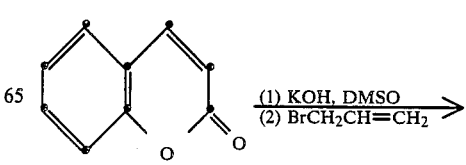

-continued

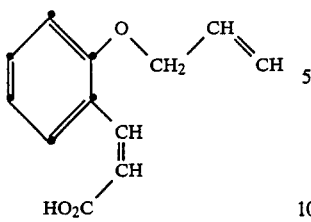

A slurry of coumarin (14.6 g, 0.10 mol) and potassium hydroxide (83 g, 1.48 mol) in 300 mL dimethyl sulfoxide was stirred at ambient temperature for 4 hours. Allyl bromide (8.66 mL, 0.10 mol) was added over 5 minutes and the reaction stirred at ambient temperature for 30 minutes. The mixture was poured into ice water, the solution filtered and then acidified (pH<3.0) with hydrochloric acid. The solid was filtered, air dried, then recrystallized from methlcyclohexane to yield cream needles (12.04 g, 59.0%), mp 80°–82° C.

Anal: (fd(calc)) C 70.6; H 6.1 (5.9).

Spectral data were consistent with the structural assignment. (This preparation follows readily from that described in the aforesaid article by S. K. Kaul in *Indian J. Chem.*)

EXAMPLE 3:

trans-3-carboxymethyl-2-vinyl-2,3-dihydrobenzo[b]furan

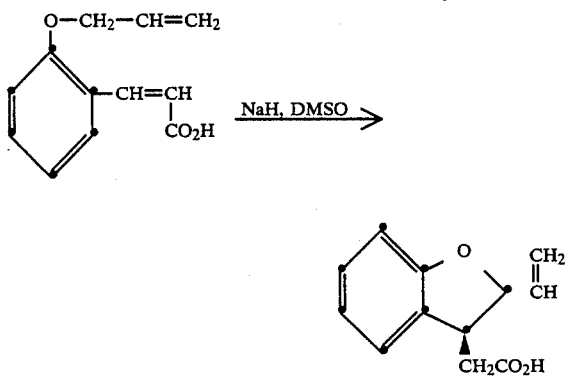

A slurry of sodium hydride (2.30 g 50% dispersion, 0.048 mol) in 50 mL dimethyl sulfoxide was warmed at 70° C. until gas evolution ceased. The solution was cooled to ambient temperature and then treated with 2'-allyloxy-Z-cinnamic acid from Preparation number 2 (2.04 g, 0.010 mol) in 10 mL dimethyl sulfoxide. After 30 minutes of cyclizing, the reaction was poured into ice water. An extractive ethyl acetate workup gave a colorless solid. Chromatography over silica gel using mixtures of ethyl acetate and methylene chloride gave a colorless solid. Recrystallization from liqroin gave colorless crystals (0.46 g, 22%) mp 79°–81° C. A second crop was obtained by recrystallization of the residue from the original mother liquors (0.20 g, total 32.4%).

Anal: (fd(calc)) C 70.9 (70.6); H 6.0 (5.9). Spectral data were consistent with the structural assignment.

EXAMPLE 4:

trans-3-Ethoxycarbonylmethyl-2-phenyl-2,3-dihydrobenzo[b]furan

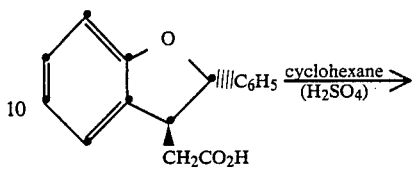

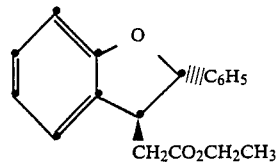

A solution of trans-caraboxymethyl-2,3-dihydrobenzofuran (4.00 g, 0.0157 mol) (Example 3), 100 mL cyclohexane, 0.5 mL concentrated sulfuric acid, and 15 mL ethanol were heated at reflux under a Soxhlet extractor charged with 3A molecular sieves. After one hour the mixture was cooled, passed through a silica gel pad with methylene chloride, then concentrated in vacuo. The residue upon trituration with ligroine gave a colorless solid (4.25 g, 96%), mp 42°–43° C.

Anal: (fd(calc)) C 76.6 (76.6); H 6.4 (6.6).

Spectral data were consistent with the assigned structure.

To the best of my knowledge, there is no procedure other than the novel cyclizing steps of this invention, that will readily produce the benzofurans of this invention. Particularly, it has not been possible prior to this invention to prepare these from compound A referred to above in the "Background of the Invention".

The invention has been described in detail with particular reference to preferred embodiments thereof, but it will be understood that variations and modifications can be effected within the spirit and scope of the invention.

What is claimed is:

1. A benzofuran having the following structural formula:

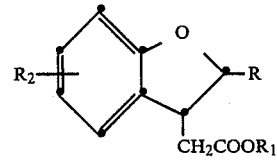

wherein R is alkenyl of 2 to 6 carbon atoms or aryl of from 6 to 10 carbon atoms; $R_1$ is H, alkali metal, or alkyl of 1 to 4 carbon atoms; and $R_2$ is alkyl or alkoxy of from 1 to 5 carbon atoms, hydrogen, amino or dialkylamino, nitro, alkyl or aryl thioether wherein the aryl group contains 6 to 10 carbon atoms, or halo.

2. The cis or trans isomer of 3-carboxymethyl-2-phenyl-2,3-dihydrobenzo[b]furan.

3. The cis or trans isomer of 3-carboxymethyl-2-vinyl-2,3-dihydrobenzo[b]furan.

4. The cis or trans isomer of 3-ethoxycarbonylmethyl-2-phenyl-2,3-dihydrobenzo[b]furan.

5. A method of forming a compound of the formula:

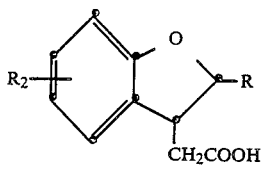

wherein R is alkenyl of 2 to 6 carbon atoms or aryl of from 6 to 10 carbon atoms; and $R_2$ is alkyl or alkoxy of from 1 to 5 carbon atoms, hydrogen, amino or dialkylamino, nitro, alkyl or aryl thioether wherein the aryl group contains 6 to 10 carbon atoms, or halo; comprising the step of cyclizing a compound of the formula:

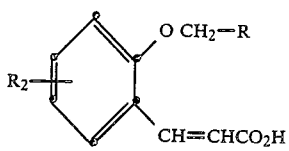

wherein R and $R_2$ are as defined above, in the presence of a base selected from the group consisting of KOH, NaOH, LiOH, dimsyl sodium, lithium diisopropylaminde, potassium tert-butoxide and mixtures thereof, at room temperature.

* * * * *

UNITED STATES PATENT AND TRADEMARK OFFICE
CERTIFICATE OF CORRECTION

PATENT NO. : 4,720,559

DATED : January 19, 1988

INVENTOR(S) : Thomas R. Welter

It is certified that error appears in the above-identified patent and that said Letters Patent are hereby corrected as shown below:

Abstract, last line, additional paragraph should read --These compounds have utility as intermediates in producing acetamidine derivatives useful as anti-hypertensive compounds.--.

Column 8, line 4, "diisopropylaminde" should read --diisopropylamide--.

Signed and Sealed this

Twenty-fourth Day of May, 1988

Attest:

DONALD J. QUIGG

Attesting Officer

Commissioner of Patents and Trademarks